United States Patent [19]
Himeno et al.

[11] Patent Number: 5,899,693
[45] Date of Patent: May 4, 1999

[54] DENTAL TIP JIG AND DENTAL TIP FITTED WITH IT

[75] Inventors: Kazuko Himeno, 1-4, Tomiokagojo 3-chome, Teine-ku, Sapporo-shi, Hokkaido; Hiroshi Himeno, Sapporo, both of Japan

[73] Assignees: Hakusui Trading Co., Ltd, Osaka, Japan; Satelec SA, Merignac Cedex, France; Kazuko Himeno, Hokkaido, Japan

[21] Appl. No.: 08/981,082
[22] PCT Filed: Apr. 11, 1997
[86] PCT No.: PCT/JP97/01270
  § 371 Date: Feb. 12, 1998
  § 102(e) Date: Feb. 12, 1998
[87] PCT Pub. No.: WO97/38644
  PCT Pub. Date: Oct. 23, 1997

[30] Foreign Application Priority Data

Apr. 12, 1996 [JP] Japan .................................. 8-091340

[51] Int. Cl.$^6$ ................................ A61C 1/07; A61C 3/03; A61C 3/08
[52] U.S. Cl. .............................................. 433/119; 433/118
[58] Field of Search ...................... 433/118, 119, 433/88, 89, 126

[56] References Cited

U.S. PATENT DOCUMENTS

| | | | |
|---|---|---|---|
| 1,992,770 | 2/1935 | Rathbun | 433/119 X |
| 3,645,255 | 2/1972 | Robinson | 433/119 X |
| 3,809,977 | 5/1974 | Balamuth et al. | 433/119 X |
| 4,176,454 | 12/1979 | Hatter et al. | 433/119 |
| 4,634,420 | 1/1987 | Spinosa et al. | 433/119 X |
| 4,731,019 | 3/1988 | Martin | 433/119 |
| 5,100,321 | 3/1992 | Coss et al. | 433/118 |

*Primary Examiner*—Nicholas D. Lucchesi
*Attorney, Agent, or Firm*—Birch, Stewart, Kolasch & Birch, LLP

[57] ABSTRACT

There is provided a substantially disposable dental tip incorporated in an ultrasonic scaler and a dental working distal end piece used for the dental tip.

The dental tip in accordance with the present invention includes a transmission medium whose proximal end portion is connected to an ultrasonic vibration source to transmit ultrasonic vibrations generated from the ultrasonic vibration source and the dental working distal end piece of the present invention which is mounted on a distal tip end of the transmission medium and consists of a tip end member having a shape suitable for dental treatment etc. and a connecting portion connected integrally to a proximal end portion of the tip end member.

4 Claims, 6 Drawing Sheets

DENTAL TIP JIG AND DENTAL TIP FITTED WITH IT

This application claims the benefit under 35 U.S.C. §371 of prior PCT International Application No. PCT/JP97/01270, which has an International filing date of Apr. 11, 1997, which designated the United States of America, the entire contents of which are hereby incorporated by references.

TECHNICAL FIELD

The present invention relates to a dental working tip end piece and a dental tip for mounting the same. More particularly, to a dental working tip end piece which is disposable after being used for dental treatment such as tooth periphery treatment, tooth inside treatment, preventive measures, and polishing.

BACKGROUND ART

Dental calculus and dental plaque are main causes for periodontal diseases and dental caries. Therefore, the removal of dental calculus and dental plaque sticking to tooth surfaces and root surfaces as well as artificial repair prosthetic appliances and dental implants is the most important measure for treatment and prevention of dental diseases.

In such dental treatment, the removal of dental calculus and dental plaque on tooth surfaces, the debridement in pockets, and the detoxification of dental root surfaces for smoothening root surfaces, that is, dental plaque control, scaling, and root planing are important basic measures.

Incidentally, scaling means an operation for removing sticking matters such as dental plaque and dental calculus above and below the gingival margin. The root planing means an operation for smoothening dental root surfaces and removing destroyed cementum and dental calculus remaining and embedded in dental root surfaces to detoxify the contaminated dental root surfaces.

The above-mentioned scaling and root planing operations are usually performed by using a hand metallic scaler, especially a hand curette scaler. At present, this method is the most reliable one in the world. However, the scaling and root planing using a hand curette scaler require very high skill and are troublesome.

Also, the scaling and root planing are sometimes done by supplementarily using a treatment appliance such as an engine Roto sonic scaler, turbine air scaler, and ultrasonic scaler besides the method using a hand curette scaler.

Among these treatment appliances, the ultrasonic scaler is designed so that a dental tip of a predetermined shape is connected to an ultrasonic vibration source for generating ultrasonic waves of a predetermined frequency. The dental tip is integral from the proximal end thereof to the distal tip end, and the proximal end can be connected detachably to the aforesaid ultrasonic vibration source.

When the ultrasonic vibration source is operated in the ultrasonic wave zone, the ultrasonic vibrations are transmitted from the proximal end to the distal tip end. By pressing the distal tip end against a portion to be treated on a tooth surface, dental calculus etc. are ground and removed.

On this ultrasonic scaler, therefore, the aforesaid tip functions as a transmission medium for ultrasonic vibrations generated by the ultrasonic vibration source.

Dental treatment includes a variety of items such as the removal of matter sticking to teeth and artificial objects (artificial dental roots, artificial teeth, artificial filling repair prosthetic appliances such as inlay and amalgam, etc.), the removal of pathological portions, the grinding and polishing of surfaces, the cleaning, the treatment of root canals, and the destroying of salivary stones.

For the tip of the aforesaid ultrasonic scaler, therefore, special-purpose tips of a shape suitable for each kind of dental treatment are usually used so that the above listed dental treatments can be provided properly. For example, a tip of a complicated shape along a tooth surface for tooth periphery treatment, a tip for prevention, a tip for the enlargement and cleaning of the interior of a root canal, a tip for filling a root canal, a tip for treatment of an inverted root canal, etc. are available.

These tips are usually manufactured as integral ones using a metallic material with high corrosion resistance and wear resistance such as stainless steel. In particular, a dental tip manufactured of a hard metallic material is a very effective tip for dental treatment because it inhibits tip wear in use and also can efficiently remove the sticking matters such as dental calculus in a short period of time. On the other hand, however, the metallic tip is liable to damage teeth and artificial objects. Once they are damaged, dental calculus, dental plaque, etc. stick to the damaged portion, by which periodontal diseases and dental caries are newly caused.

The metallic tip is generally connected to the ultrasonic vibration source using screw threads in order not only to reliably transmit ultrasonic vibrations to the tip and but also to prevent the tip from coming off during use by securely fixing the tip.

When the mode of dental treatment is changed, it is necessary to do replacement work such that the mounted tip is disconnected from the ultrasonic vibration source by screwing to remove the tip. Thereafter and then another tip of a shape suitable for the dental treatment to be given next is connected to the ultrasonic vibration source by screwing. That is to say, each time the mode of dental treatment is changed, work is necessary for removing the tip having been used and mounting a new tip by screwing.

However, such work requires a special-purpose mounting/demounting tool. Also, from the standpoint of a dentist who actually provides dental treatment, the time required for tip replacement is an ineffective time and the replacement work is troublesome, and also the ultrasonic scaler cannot be used efficiently.

The tip end is formed with a small-diameter water passage extending in the shank from the proximal end to the distal tip end. This passage is actually used for spraying cleaning water or liquid medicine from the water passage when dental treatment is provided. However, since the tip itself is complicated and thin in shape, the work for forming the above-mentioned water passage requires a high level of skill. As a result, it is difficult to mass-produce the tips at a low cost. For this reason, the price of the dental tip is necessarily very high.

On the other hand, in recent years, in order to avoid infections from diseases such as AIDS and serum hepatitis which have a strong infectivity when dental treatment is given, an apparatus used for treatment, especially an apparatus which comes into direct contact with a secretion such as saliva and blood, or an apparatus which comes into direct contact with the secretion and moreover has a small hole, has been desired to be disposable.

However, since the conventional dental tip is very expensive as described above, it cannot be thrown away after each dental treatment.

Further, when a person attempts to remove dental calculus for prevention, or to polish the tooth surfaces by himself, the tip cannot be thrown away all the more because the tip is expensive.

SUMMARY AND OBJECTS OF THE INVENTION

An object of the present invention is to solve the above problems with a dental tip used for an ultrasonic scaler, and to provide a dental working tip end piece which effectively works at a treatment place when the ultrasonic scaler is operated for tooth periphery treatment, tooth inside treatment, preventive measures, polishing measure, and the like (hereinafter referred to as dental treatment). The dental tip end piece can be mounted/demounted easily by the motion of a single finger, and moreover is disposable after the treatment is finished because it can be manufactured at a low cost. In addiction a dental tip is provided to which the dental working tip end piece is mounted.

The inventors carried on studies to achieve the above object, and noticed, in the course of the studies, that a conventional dental tip, from a proximal end to which ultrasonic vibrations are introduced to a distal tip end which gives actual dental treatment etc. by using the ultrasonic vibrations, is formed of a predetermined material, being an integral object of a complicated shape.

For the practically used dental tip, only the distal tip end portion occupying a small portion of the whole is a working portion for achieving the actual dental treatment etc., and most of other portions merely function as a transmission medium for transmitting ultrasonic vibrations to the distal tip end portion (working portion).

For this reason, if an attempt is made to throw away the distal tip end portion after being used for the actual dental treatment etc., the transmission medium which can still be used for a long period of time must also be thrown away at the same time.

Considering the above fact, the inventors developed the idea that in the dental tip, the distal tip end portion effectively working at an area of treatment and the transmission medium for ultrasonic vibrations should be formed separately so that the distal tip end portion can be mounted/demounted detachably by the motion of a single finger, whereby a substantially disposable dental tip can be provided by throwing away only the distal tip end portion after the dental treatment etc. is finished, and consequently developed the dental working distal tip end piece of the present invention and the dental tip mounting the same.

That is, the present invention provides a dental working tip end piece having a shape suitable for dental treatment, which is mounted detachably on a distal tip end of a transmission medium for ultrasonic vibrations.

In particular, the present invention provides a dental working distal end piece in which a portion mounted on the distal tip end of the transmission medium is a connecting portion made of a plastic material.

Also, the present invention provides a dental tip comprising:

- a transmission medium, which is connected to an ultrasonic vibration source, for transmitting ultrasonic vibrations generated from the ultrasonic vibration source; and
- a dental working tip end piece having a shape suitable for dental treatment etc., which is detachably mounted on a distal tip end of the transmission medium.

In particular, the present invention provides a dental tip in which the dental working tip end piece has a bottomed hole or through hole into which the distal tip end of the transmission medium can be inserted, a protrusion is formed on the surface of the distal tip end of the transmission medium and a recess corresponding to the protrusion is formed on the inner wall of the bottomed hole or through hole, and at least a part of the surface of the distal tip end of the transmission medium is embeded with diamonds.

BEST MODE OF CARRYING OUT THE INVENTION

Figure 1:
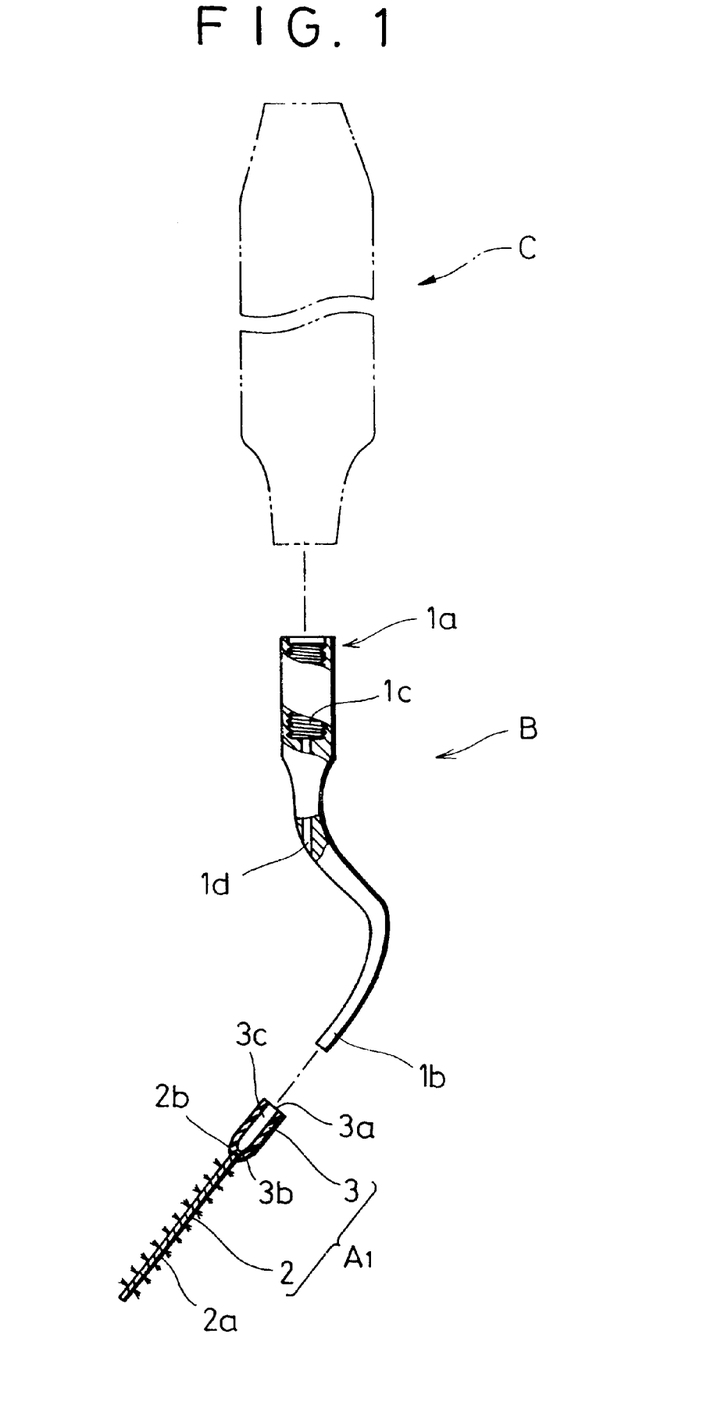
FIG. 1 is an exploded view showing an example of a dental tip to which a dental working tip end piece $A_1$ in accordance with the present invention is mounted.

FIG. 1 is an exploded view showing an example of an ultrasonic scaler in which a dental tip of the present invention is incorporated.

In FIG. 1, a dental tip of the present invention is formed by connecting a dental working tip end piece $A_1$, described later, to a transmission medium B, also described later. The dental tip is connected to an ultrasonic vibration source C such as a hand piece.

The transmission medium B shown in FIG. 1 has conventionally been used as a dental tip. For example, the entire shape of the transmission medium B is curved complicatedly longitudinally and laterally along the dental root surface from a proximal end 1a to a distal tip end 1b, and the entire structure is manufactured integrally.

Internal threads 1c, for example, is formed at the proximal end portion 1a of the transmission medium B, and external threads (not shown) are formed at the tip end of the ultrasonic vibration source C and are engaged with the internal threads 1c. Thereby, the transmission medium B is connected to the ultrasonic vibration source C to transmit ultrasonic vibrations. Also, a water passage 1d is formed along the axis of the proximal end portion 1a and opens at a halfway position of the transmission medium B so that cleaning water or liquid medicine is sprayed from this opening. The distal tip end 1b of the transmission medium B has a wire shape having a desirable diameter and length.

In actual dental treatment, the transmission medium B merely transmits ultrasonic vibrations from the ultrasonic vibration source C to the distal tip end 1b, and does not come in direct contact with a portion to be treated such as a tooth, artificial object, or root canal. Therefore, the transmission medium B may be manufactured of a material capable of transmitting ultrasonic vibrations effectively. Also, the shape of transmission medium B is not subject to any special restrictions, and the transmission medium B may be manufactured into an arbitrary suitable shape, and the manufacturing conditions may be selected relatively freely.

Specifically, the transmission medium B may be manufactured of a hard material as before, or may be manufactured of a material for which application has already been filed by the inventors as set forth in Japanese Patent Application No. 7-330867, that is, a composite material consisting of a matrix of plastic material and a reinforcing material of inorganic and/or organic filler blended in the matrix.

A dental working tip end piece $A_1$ for dental treatment in accordance with the present invention is mounted on the distal tip end 1b of the transmission medium B.

The dental working tip end piece $A_1$ of the present invention shown in FIG. 1 is formed of an integral piece comprising a tip end member 2 consisting of a working portion 2a of a shape suitable for treatments such as tooth periphery treatment, tooth inside treatment, polishing, and prevention. A connecting portion 3 is made of a plastic material.

The connecting portion 3 has a shape of a pipe piece whose one end is closed, and a bottomed hole 3c with a diameter slightly smaller than the diameter of the distal tip end 1b of the aforesaid transmission medium B is formed from one end 3a of the connecting portion 3 to a closed end 3b thereof. To the closed end 3b, a proximal end portion 2b of the aforesaid tip end member 2 is integrally connected. This integral connection between the tip end member 2 and the connecting portion 3 can be made easily by applying molding technology used for a plastic material.

Specifically, a plastic material may be injection molded, for example, in a state in which the proximal end portion 2b of the tip end member 2, which has been manufactured separately, is arranged at the place corresponding to the closed end 3b of the face of a mold which can mold the connecting portion 3. The proximal end portion 2b of the tip end member 2 is integrated with the connecting portion 3 with the proximal end portion 2b being embedded in the closed end 3b of the molded connecting portion 3.

The material forming the tip end member 2 of the working tip end piece $A_1$ may be a metallic material, or may be a metallic material having diamond, brush, rubber, etc. attached onto the surface thereof.

Also, the material may be wood or a plastic material with relatively high hardness and modulus of elasticity, or may be a composite material for which an application has been filed as set forth in the above-mentioned Japanese Patent Application No. 7-330867.

Considering that the tip end portion 2 of the working tip end piece $A_1$ is directly pressed against a portion to be treated in actual dental treatment, the tip end portion 2 should preferably be formed of a material which does not damage the portion to be treated.

When the tip end member 2 is formed of a plastic material or the aforesaid composite material, an abrasive material consisting of fine powders of alumina, silica, zirconia, glass, silicon carbide, boron carbide, diamond, etc. is blended in the plastic material during molding, or attached onto the surface. This process is useful because the polishing effect is improved. If the working tip end piece $A_1$ is formed by arranging chips of abrasive substance such as metal chips, ceramic chips, and glass chips at the distal end of the tip end member 2, the cutting effect is also improved.

This working tip end piece $A_1$ is actually used by mounting the connecting portion 3 on the distal tip end 1b of the transmission medium B.

Specifically, the distal tip end 1b of the transmission medium B is inserted into the bottomed hole 3c through the proximal end 3a of the connecting portion 3 of the working tip end piece $A_1$. The bottomed hole 3c of the connecting portion 3 has a diameter slightly smaller than the diameter of the distal tip end 1b of the transmission medium B, and the connecting portion 3 is formed of a plastic material relatively softer than the material (usually a metal) of the transmission medium B. Therefore, the distal tip end 1b of the transmission medium B is pressed into contact with the peripheral wall of the connecting portion 3, being held without play.

As a result, the working tip end piece $A_1$ is connected to the transmission medium B via the connecting portion 3, by which the dental tip is formed.

When the dental tip is connected to the ultrasonic vibration source C to introduce predetermined ultrasonic vibrations to the transmission medium B, the ultrasonic vibrations are transmitted from the proximal end portion 1a to the distal tip end 1b of the transmission medium B, and further transmitted to the working portion 2a of the tip end member 2 via the connecting portion 3 of the working tip end piece $A_1$. As a result, the working portion 2a accomplishes predetermined dental treatment.

After the dental treatment is finished, the connecting portion 3 of the working tip end piece $A_1$ is disconnected from the distal tip end 1b of the transmission medium B. Specifically, only the used working tip end piece $A_1$ can be separated by pulling it out of the distal tip end 1b, and thrown away. For the next dental treatment, the transmission medium B is reused, and a new working tip end piece $A_1$ of a shape suitable for the new dental treatment may be mounted on the distal tip end 1b in the same manner as described before.

Also, when various treatments are given by changing a tip suitable for each treatment, in the present invention, the intended treatments can be carried on efficiently using clean working tip end pieces by preparing working tip end pieces of a shape suitable for each treatment in advance and by successively mounting and demounting the working tip end piece to and from the transmission medium B.

The important point of the dental tip shown in FIG. 1 is that the ultrasonic vibrations reaching the distal tip end 1b through the transmission medium B are positively transmitted to the tip end member 2 of the working tip end piece $A_1$ via the connecting portion 3.

For this purpose, the distal tip end 1b of the transmission medium B should preferably be in close contact with the inner wall of the connecting portion 3. Also, the connecting portion 3 should preferably have a property such that the connecting portion 3 resonates with the frequency of the ultrasonic vibrations transmitted through the transmission medium B.

In particular, when the ultrasonic scaler is used safely, it is preferable that the power thereof should be as low as possible. In this case, since the vibration power is low, the above-mentioned point is very important to positively transmit the vibration power to the working portion 2a.

Generally, for a plastic material, the ultrasonic vibrations transmitted therethrough are damped greatly as compared with the case of metallic material. In the case of the dental tip of the present invention as well, therefore, the ultrasonic vibrations are damped at the connecting portion 3 because the connecting portion 3 is made of a plastic material, so that sometimes they are not transmitted enough to the tip end portion 2 and, in turn, to the working portion 2a.

To overcome such a problem, the connecting portion 3 of plastic material is configured so as to be in the best condition for the working tip end piece $A_1$ to operate by appropriately selecting the property of the plastic material forming the connecting portion 3, inside diameter, length, and thickness of the connecting portion 3. Thereby, the transmission efficiency of the ultrasonic vibrations to the working portion $2a$ of the working tip end piece $A_1$ can be controlled to be suitable.

In this case, it is preferable that the connecting portion 3 is formed of the composite material for which application is applied by the inventors as set forth in Japanese Patent Application No. 7-330867.

This is because, for this composite material, the natural frequency thereof can be adjusted finely by changing the type and combination of the matrix and the reinforcing material filled therein, by changing the filling ratio of reinforcing material, or by appropriately selecting the shape, so that the connecting portion 3 is allowed to resonate in response to the frequency even if the frequency of the ultrasonic vibrations transmitted to the distal tip end $1b$ of the transmission medium B varies.

In other words, the connecting portion 3 can be manufactured so as to have the optimum natural frequency.

If the surface of the distal tip end $1b$ of the transmission medium B is made, for example, a pear-skin-like surface by being embedded with a hard material such as diamond and SiC, the hard material bites into the inner wall of the connecting portion 3 to be immobilized when the working tip end piece $A_1$ is fitted on the distal tip end $1b$, so that the connecting (contacting) condition between the distal tip end $1b$ of the transmission medium B and the working tip end piece $A_1$ is improved. As a result, the transmission efficiency of the ultrasonic vibrations to the tip end portion 2 is improved.

In this case, the entire surface or partial surface of the distal tip end $1b$ may be embedded with the hard material.

In effect, the surface of the distal tip end $1b$ should be embedded so as to establish a connecting condition in which the distal tip end $1b$ is in close contact with the inner wall of the connecting portion 3 by increasing the contacting area between the distal tip end $1b$ and the inner wall of the connecting portion 3.

Figure 2:
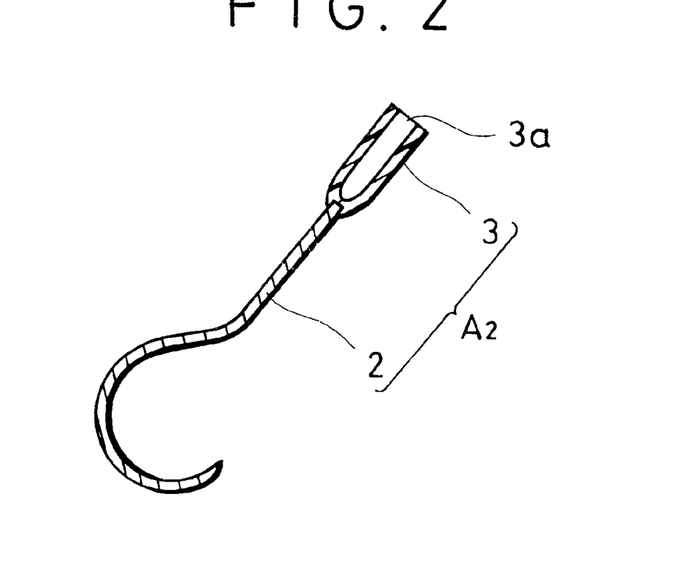
FIG. 2 is a sectional view showing another dental working tip end piece $A_2$ in accordance with the present invention.

FIG. 2 shows another dental working tip end piece $A_2$ in accordance with the present invention. This working tip end piece $A_2$ has the tip end portion 2 of a metallic hook shape suitable for tooth periphery treatment, and the tip end portion 2 is integrated with the connecting portion 3. Like the working tip end piece $A_1$, this working tip end piece $A_2$ is actually used by inserting the distal tip end of the transmission medium (not shown) into the tip end $3a$ of the connecting portion 3. When the working tip end piece $A_2$ is removed, it is only necessary that it is pulled out.

Figure 3:
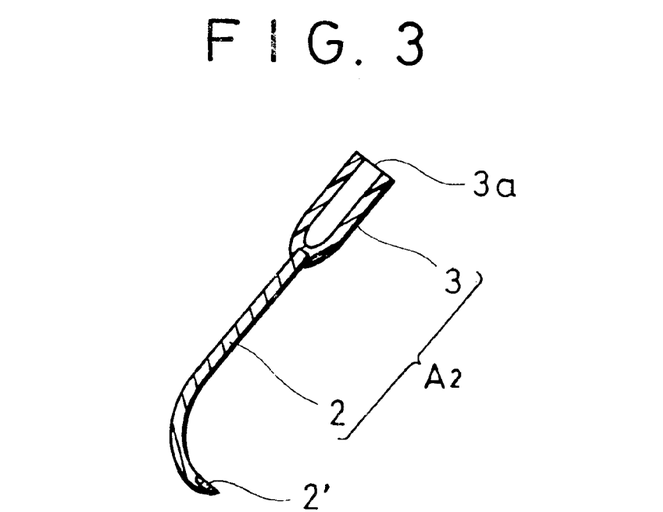
FIG. 3 is a sectional view showing a modification of the dental working end tip piece $A_2$.

If a chip $2'$ of abrasive substance is arranged at the tip end of the tip end portion as shown in FIG. 3, the cutting effect is further improved.

Figure 4:
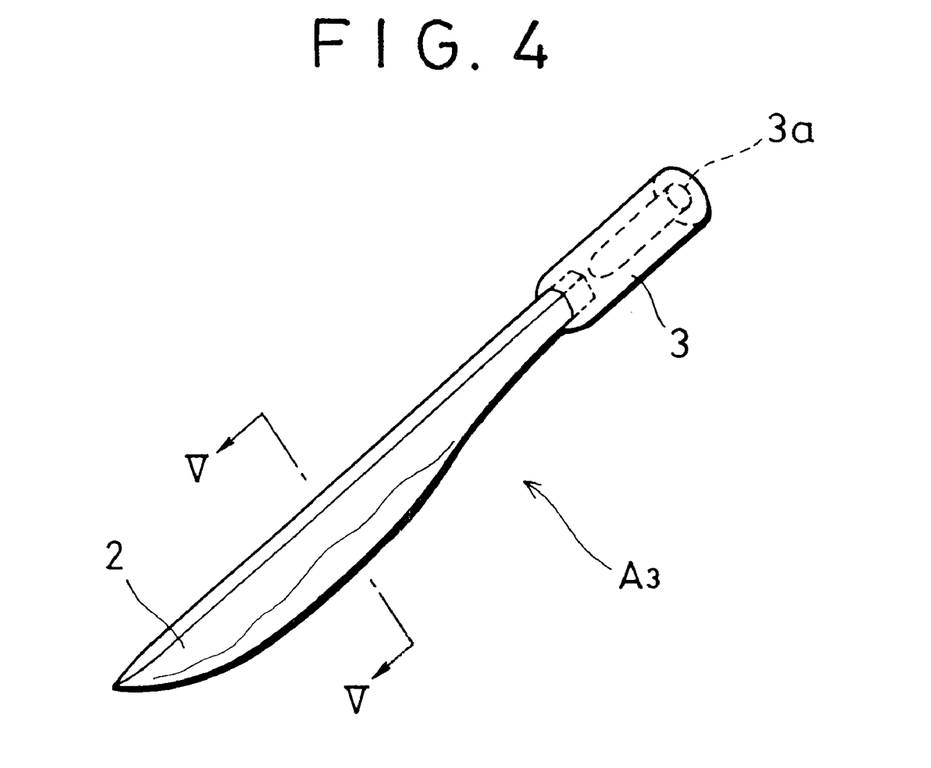
FIG. 4 is a perspective view of still another dental working end tip piece $A_3$.
Figure 5:
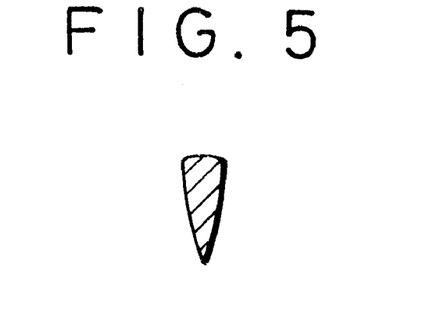
FIG. 5 is a sectional view taken along the line V—V of FIG. 4.

FIG. 4 and FIG. 5, which is a sectional view taken along the line V—V of FIG. 4, show still another dental working tip end piece $A_3$ in accordance with the present invention. The tip end portion 2 of this working tip end piece $A_3$ is formed of a plastic material or wood, and has a butcher knife shape matching the space between teeth. The proximal end of the tip end portion 2 is integrated with the connecting portion 3 formed of a plastic material. This working tip end piece $A_3$ is also actually used by inserting the distal tip end of the transmission medium into the tip end $3a$ of the connecting portion 3.

Figure 6:
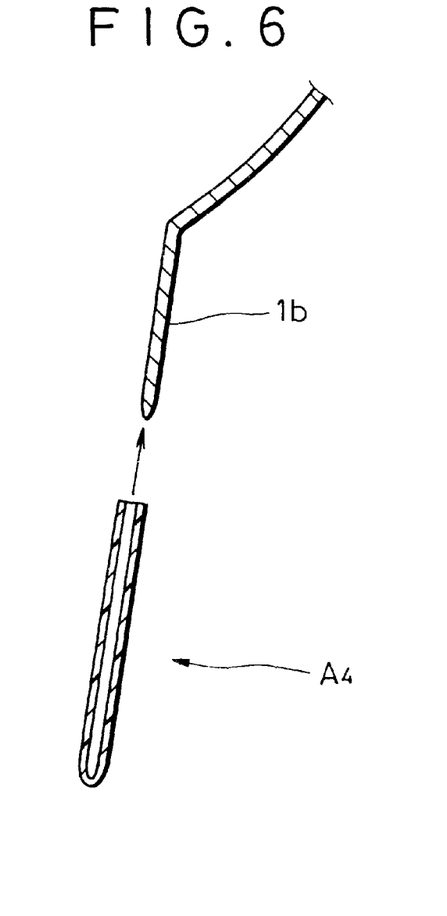
FIG. 6 is a sectional view of still another dental working tip end piece $A_4$ in accordance with the present invention.

FIG. 6 shows still another dental working tip end piece $A_4$ in accordance with the present invention. This working tip end piece $A_4$ is formed of a plastic material as a whole, and has a sheath shape. This working tip end piece $A_4$ is actually used by putting it on the distal tip end $1b$ of the transmission medium, and after use, it is removed from the distal tip end $1b$ and thrown away. The working tip end piece $A_4$ is used, for example, when a person removes his dental calculus or tar sticking to the tooth surfaces by himself. To achieve the polishing effect, an abrasive substance may be mixed with the plastic material. Since the whole of the working tip end piece $A_4$ is formed of a plastic material, safety can be secured even by a nonprofessional. Further, by being formed of a soft plastic material with flexibility, it can accommodate any shape of the distal tip end $1b$ of the transmission medium.

Figure 7:
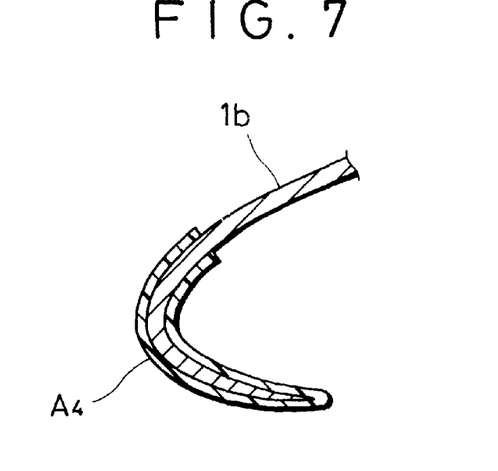
FIG. 7 is a sectional view showing another example of the dental working tip end piece $A_4$.

Even if the distal tip end $1b$ of the transmission medium is curved, for example, as shown in FIG. 7, the working tip end piece $A_4$ can be actually used by being deformed freely so as to match the shape of the distal tip end $1b$.

Figure 8:
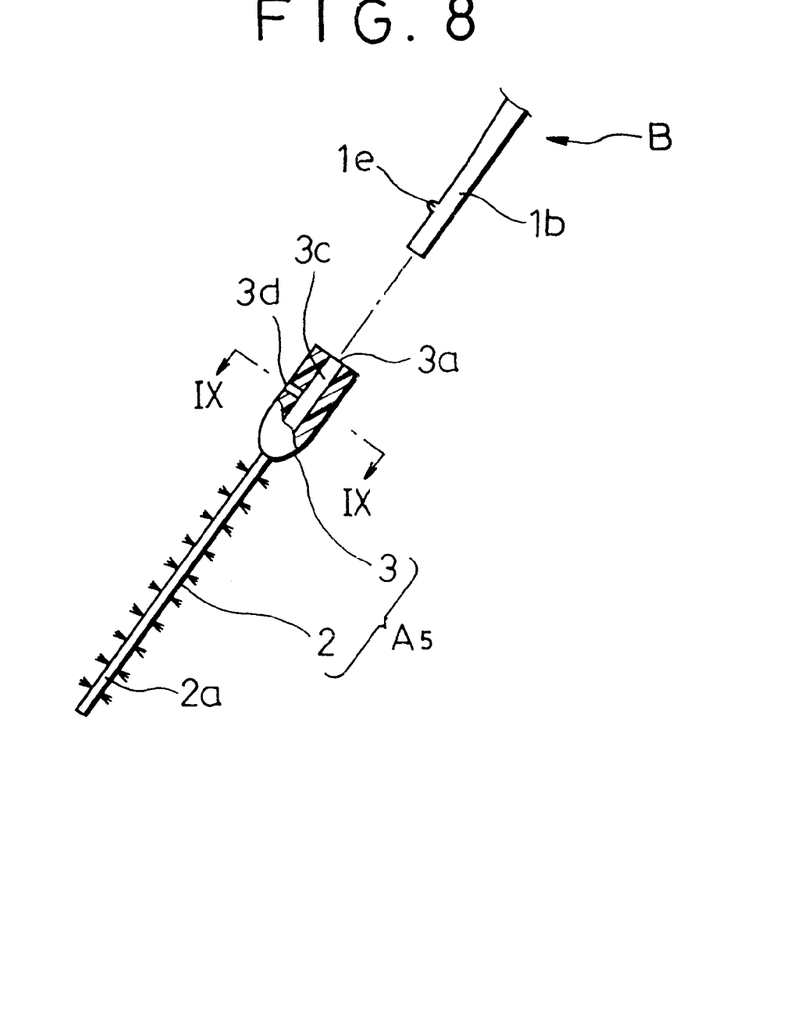
FIG. 8 is a partially broken view of still another dental working tip end piece $A_5$ in accordance with the present invention.
Figure 9:
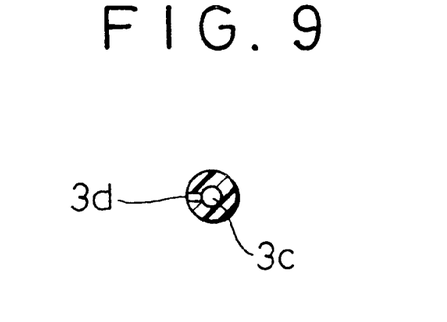
FIG. 9 is a sectional view taken along the line IX—IX of FIG. 8.

FIG. 8 and FIG. 9, which is a sectional view taken along the line IX—IX of FIG. 8, show still another dental working tip end piece $A_5$ in accordance with the present invention.

For this working tip end piece $A_5$, a small hole $3d$ is formed as a recess on the wall surface of the bottomed hole $3c$ of the working tip end piece $A_1$ shown in FIG. 1. At the distal tip end $1b$ of the transmission medium B, which is inserted into the bottomed hole $3c$, a small protrusion $1e$ having almost the same diameter as that of the small hole $3d$ is formed.

When this working tip end piece $A_5$ is actually used, the working tip end piece $A_5$ is fitted on the distal tip end $1b$ of the transmission medium B, and turned slightly to the right or left if necessary. When the protrusion $1e$ of the distal tip end $1b$ aligns with the position of the small hole $3d$ of the connecting portion 3, the protrusion $1e$ fits in the small hole $3d$, and the working tip end piece $A_5$ is integrated with the transmission medium B, by which the dental tip is formed. For the dental tip thus formed, since the protrusion $1e$ fits in the small hole $3d$, the working tip end piece $A_5$ won't come off from the transmission medium B when the tip is operated.

In order to remove the working tip end piece $A_5$, it is only necessary that the working tip end piece $A_5$ is pulled out of the distal tip end $1b$ of the transmission medium as it is. The pulling-out work is easy because the protrusion $1e$ of the distal tip end $1b$ is small in shape, and the connecting portion 3 is formed of a plastic material having elasticity.

Figure 10:
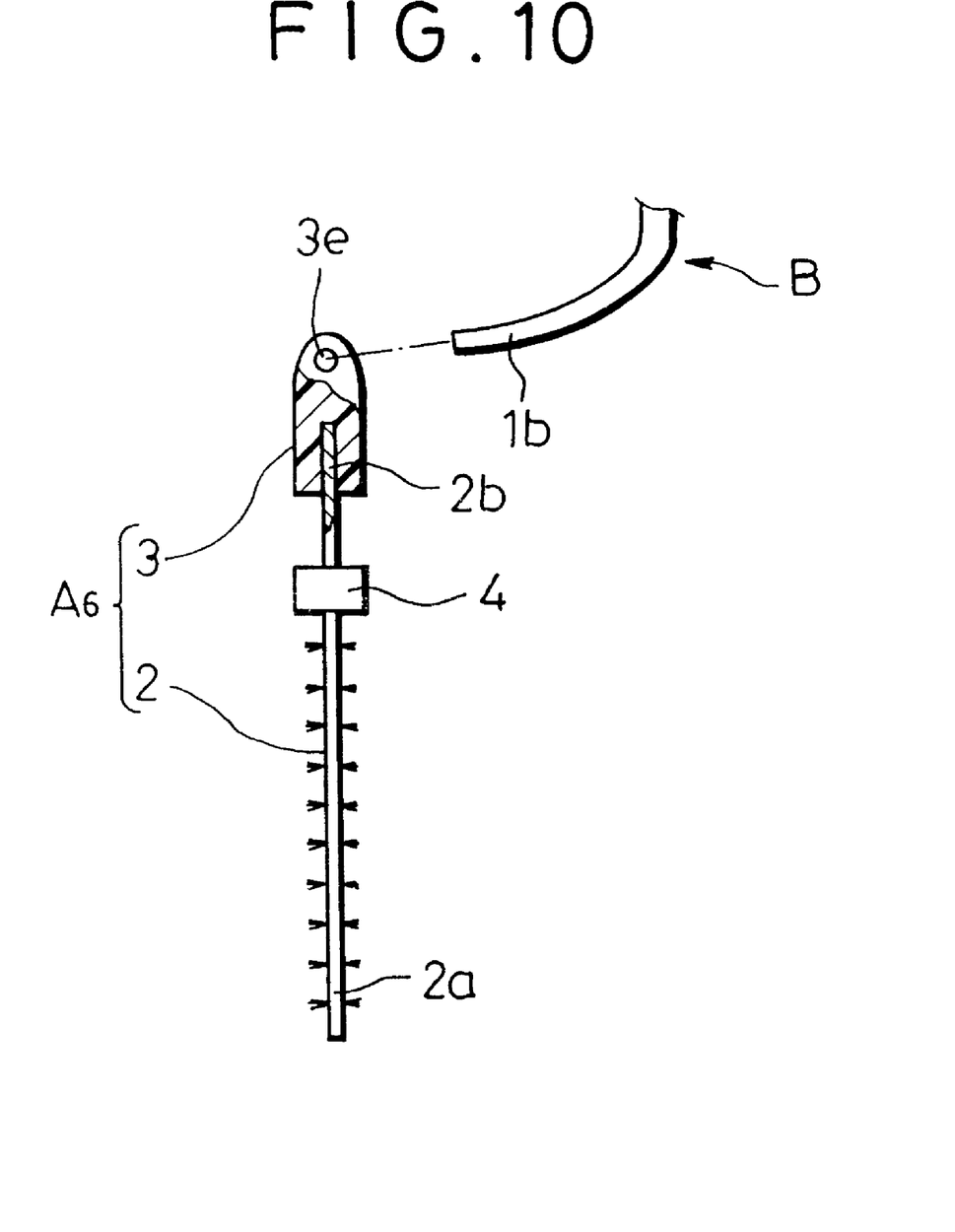
FIG. 10 is a partially broken view of still another dental working end tip piece $A_6$ in accordance with the present invention.

FIG. 10 shows still another dental working tip end piece $A_6$ in accordance with the present invention, which can be used as a reamer file.

For this working tip end piece $A_6$, a marker 4, which is an index for the distance to a dental nerve, is installed to the tip end member 2, and the proximal end portion $2b$ thereof is integrated with the connecting portion 3 formed of a plastic material. At the upper part of the connecting portion 3 is formed a through hole $3e$ having a diameter slightly smaller than that of the distal tip end $1b$ of the transmission medium B.

This through hole $3e$ may be formed at any position of the connecting portion 3, which can avoid the position of the proximal end portion $2b$ of the tip end member 2.

When the working tip end piece $A_6$ is actually used, it is only necessary to insert the distal tip end $1b$ of the transmission medium B is inserted into the through hole $3e$. When being removed, it is only necessary that the distal tip end $1b$ is pulled out.

When the dental tip is formed using the above-described working tip end piece $A_2$, $A_3$, $A_4$, $A_5$, or $A_6$, if hard particles of, for example, diamond are embedded into the surface of the distal tip end 1b of the transmission medium B, which is the mating member for mounting, as explained regarding the working tip end piece $A_1$, the connecting condition between the distal tip end 1b and the working tip end piece becomes better, so that the transmission efficiency of ultrasonic vibrations is improved.

Also, for any type of working tip end piece, like the case of the working tip end piece $A_5$, a recess may be formed on the wall surface of hole, and a protrusion fitting in the recess may be provided at the distal tip end of the transmission medium, which is the mating member.

In the case of the dental working tip end pieces $A_1$, $A_2$, $A_3$, $A_4$, $A_5$, and $A_6$, the distal tip end 1b of the transmission medium B is inserted into the hole of the connecting portion 3 to provide a detachable connection between the transmission medium and the working tip end piece. However, the present invention is not limited to these modes. For example, the distal tip end 1b of the transmission medium may be screwed in the connecting portion 3 by screw threads, or the distal tip end 1b may be connected to the connecting portion 3 detachably by using a fit joint system. In this case, although the mounting/demounting work is troublesome, and an ineffective time occurs, the connecting condition of the two elements is firm and reliable, so that the working tip end piece won't come off during treatment. Therefore, the safety is very high.

INDUSTRIAL APPLICABILITY

The dental tip in accordance with the present invention comprises the transmission medium, which is connected to the ultrasonic vibration source, for transmitting ultrasonic vibrations and the working tip end piece having a shape suitable for dental treatment, which is detachably mounted to the distal tip end of the transmission medium. Therefore, for the dental tip of the present invention, only the working tip end piece can be removed selectively from the transmission medium and thrown away after dental treatment etc. are finished, and another working tip end piece having a shape suitable for the next dental treatment can be mounted to the transmission medium to provide the next treatment. That is to say, the dental tip in accordance with the present invention is substantially disposable.

For any one of the working tip end pieces $A_1$, $A_2$, $A_3$, $A_4$, $A_5$, and $A_6$ in accordance with the present invention, the working tip end piece can be fitted on the distal tip end 1b of the transmission medium B by the motion of a single finger, and also can be removed by being pulled out. Therefore, even if the mode of dental treatment is changed, the work in which the working tip end piece being used is removed and a working tip end piece suitable for the dental treatment to be given next is mounted to the transmission medium B can be done in a short period of time. That is to say, since the working tip end piece can be replaced easily, high treatment efficiency can be achieved.

Since the working tip end piece in accordance with the present invention can be manufactured by, for example, injection molding the tip end member, which has been manufactured in advance, and the plastic material, mass-production is possible, the manufacturing cost is low. As a result, the requirement for being disposable can be met sufficiently.

If the connecting portion is formed of the aforesaid composite material, the transmission of ultrasonic vibrations from the transmission medium can be controlled, so that the dental treatment can be given under the optimum condition.

We claim:

1. A dental tip comprising:

a transmission medium having a distal tip end and a proximal end adjusted to be connected to an ultrasonic vibration source, for transmitting ultrasonic vibrations generated from said ultrasonic vibration source; and a dental working tip end piece adapted to be detachably mounted on the distal tip end of said transmission medium;

wherein said transmission medium includes a protrusion formed on the peripheral surface of the distal tip end, and diamond particles embedded in at least a part of said peripheral surface of the distal tip end;

said dental working tip end piece consists of a plastic connecting portion and a tip end portion of a shape suitable for dental treatment, said plastic connecting portion having a bottomed hole extending in the longitudinal direction of said dental working tip end piece and adapted to having the distal tip end of said transmission medium fitted in, and a hole formed in the inner wall of said plastic connecting portion for engaging said protrusion therein.

2. The dental tip according to claim 1, wherein said connecting portion of said dental working tip end piece has a through hole extending in the radial direction of said dental working tip end piece and adapted to have a said distal tip end of said transmission medium fitted therein.

3. A dental tip comprising:

a transmission medium having a distal tip end and a proximal end adjusted to be connected to an ultrasonic vibration source, for transmitting ultrasonic vibrations generated from said ultrasonic vibration source; and a dental working tip end piece adapted to be detachably mounted on the distal tip end of said transmission medium;

wherein said transmission medium includes a recess formed on the peripheral surface of the distal tip end, and diamond particles embedded in at least a part of said peripheral surface of the distal tip end;

said dental working tip end piece consists of a plastic connecting portion and a tip end portion of a shape suitable for dental treatment, said plastic connecting portion having a bottomed hole extending in the longitudinal direction of said dental working tip end piece and adapted to having the distal tip end of said transmission medium fitted in, and a protrusion formed in the inner wall of said plastic connecting portion for engaging said recess therein.

4. The dental tip according to claim 3, wherein said connecting portion of said dental working tip end piece has a through hole extending in the radial direction of said dental working tip end piece and adapted to have a said distal tip end of said transmission medium fitted therein.

* * * * *